United States Patent
Machen et al.

(10) Patent No.: US 12,403,084 B2
(45) Date of Patent: Sep. 2, 2025

(54) CLEANSING COMPOSITION

(71) Applicant: Conopco, Inc., Englewood Cliffs, NJ (US)

(72) Inventors: Robert Machen, Wirral (GB); Arash Mojaher Moghadam, Wirral (GB); Joseph Muscat, Warrington (GB); Robert George Riley, Chester (GB); Pierre Starck, Chester (GB)

(73) Assignee: Conopco, Inc., Englewood Cliffs, NJ (US)

( * ) Notice: Subject to any disclaimer, the term of this patent is extended or adjusted under 35 U.S.C. 154(b) by 635 days.

(21) Appl. No.: 17/618,138

(22) PCT Filed: Jun. 16, 2020

(86) PCT No.: PCT/EP2020/066615
§ 371 (c)(1),
(2) Date: Dec. 10, 2021

(87) PCT Pub. No.: WO2020/254318
PCT Pub. Date: Dec. 24, 2020

(65) Prior Publication Data
US 2022/0233427 A1 Jul. 28, 2022

(30) Foreign Application Priority Data

Jun. 21, 2019 (EP) .................................... 19181766

(51) Int. Cl.
*A61K 8/73* (2006.01)
*A61K 8/06* (2006.01)
(Continued)

(52) U.S. Cl.
CPC ............. *A61K 8/891* (2013.01); *A61K 8/062* (2013.01); *A61K 8/44* (2013.01); *A61K 8/466* (2013.01);
(Continued)

(58) Field of Classification Search
None
See application file for complete search history.

(56) References Cited

U.S. PATENT DOCUMENTS 11,969,495 B2 * 4/2024 Galpin ...................... A61K 8/44
2004/0234483 A1 11/2004 Peffly et al.
(Continued)

FOREIGN PATENT DOCUMENTS

| CN | 1794969 | 6/2006 |
| CN | 101336104 | 12/2008 |

(Continued)

OTHER PUBLICATIONS

Mintel, GNPD Database (Online) "Deep Moisturizing Shampoo," McBride Research Laboratories May 2019; pp. 1-3, Record ID 6567877; United States of America.
Search Report in EP16178241; Sep. 16, 2016; European Patent Office (EPO).
Search Report and Written Opinion in PCTEP2017066523; Oct. 26, 2017; World Intellectual Property Org. (WIPO).
Search Report and Written Opinion in EP17195899; Dec. 1, 2017; European Patent Office (EPO).
Vethamuthu et al.; Fragrance Retention, Release and Sensory Perception from Surfactant-Rich Rinse-Off Cosmetics; Kirk-Othmer Chemical Technology of Cosmetics; Jan. 1, 2012; pp. 1-27; XP55426379; Ashland; United States of America.
Search Report and Written Opinion in EP17209538; Apr. 19, 2018; European Patent Office (EPO).
(Continued)

*Primary Examiner* — Brian Gulledge
(74) *Attorney, Agent, or Firm* — Carter, DeLuca & Farrell LLP; George Likourezos; Bret P. Shapiro

(57) ABSTRACT

An aqueous, sulphate free shampoo composition for hair and scalp comprising:—a. a pre-formed emulsified silicone; b. a cationic deposition polymer; c. a hair substantive cationic conditioning polymer which is an APTAC polymer having a molecular weight of less than 1 million Daltons, preferably selected from a homopolymer of (3-acrylamidopropyl) trimethyl ammonium chloride and a (3-acrylamidopropyl) trimethyl ammonium chloride/acrylamide copolymer; d. a total amount of anionic surfactant, amphoteric surfactant and zwitterionic surfactant consisting of: (i) from 3 wt % to 13 wt %, by weight of the total composition at 100% activity, of an alpha olefin sulfonate anionic surfactant of general formula (I): $R^1$—CH=CH—$CH_2$—$SO_3^{-M+}$(I) in which $R^1$ is selected from linear or branched alkyl groups having from 11 to 13 carbon atoms and mixtures thereof; and M is a solubilizing cation; (ii) from 1 to 6%, by weight of an amphoteric or zwitterionic surfactant, selected from an alkyl betaine of general formula (II) $R^2$—$N^+(CH_3)_2$—$CH_2$—$COO^-M^+$(II) wherein $R^2$=C12 (Lauryl) or Coco derived; an alkyl hydroxy sultaine of general formula (III), $R^3$—$N^+(CH_3)_2$—$CH_2$—CH(OH)—$CH_2$—$SO_3M^+$(III) wherein $R^3$=C12 (Lauryl) or Coco derived; an alkyl aminopropyl hydroxy sultaine of general formula (IV), $R^4$—CO—NH—$(CH_2)_3$—$N^+(CH_3)_2$—$CH_2$—CH(OH)—$CH_2$—$SO_3^-M^+$(IV) wherein $R^4$=C12 (Lauryl) or Coco derived; an alkyl amphoacetate of general formula (V), $R^5$—CO—NH—$(CH_2)_2$—$N(CH_2$—$CH_2$—OH)($CH_2$—$COO^-M^+$) (V) wherein $R^5$=C12 (Lauryl) or Coco derived; and mixtures thereof; and e. a suspending agent in which the weight ratio of (i) to (ii) ranges from 1:1 to 6:1 and the pH of the composition is from 3 to 6.5; and wherein the composition has a viscosity from 3,500 to 15,000 mPa·s, preferably from 4,000 to 12,000 mPa·s when measured using a Brookfield V2 viscometer using a spindle RTV5, for 1 minute at 20 rpm at 30° C. results in superior deposition and retention of silicone on hair.

18 Claims, No Drawings

(51) Int. Cl.
*A61K 8/44* (2006.01)
*A61K 8/46* (2006.01)
*A61K 8/81* (2006.01)
*A61K 8/89* (2006.01)
*A61K 8/891* (2006.01)
*A61Q 5/02* (2006.01)
*A61Q 5/12* (2006.01)

(52) U.S. Cl.
CPC ............... *A61K 8/737* (2013.01); *A61Q 5/02* (2013.01); *A61K 2800/30* (2013.01); *A61K 2800/48* (2013.01)

(56) References Cited

U.S. PATENT DOCUMENTS

| | | | |
|---|---|---|---|
| 2007/0280976 | A1 | 12/2007 | Taylor et al. |
| 2009/0197784 | A1 | 8/2009 | Ainger et al. |
| 2011/0002868 | A1 | 1/2011 | Bierganns et al. |
| 2011/0048449 | A1 | 3/2011 | Hutton, III et al. |
| 2012/0076747 | A1* | 3/2012 | Bierganns ............. C11D 1/345 424/70.13 |
| 2012/0276210 | A1 | 11/2012 | Dihora et al. |
| 2013/0108571 | A1 | 5/2013 | Adamy |
| 2013/0209388 | A1 | 8/2013 | Erazo-Majewicz et al. |
| 2013/0296289 | A1 | 11/2013 | Hall et al. |
| 2014/0079658 | A1 | 3/2014 | Terazaki et al. |
| 2016/0045417 | A1 | 2/2016 | Schroeder et al. |
| 2017/0151145 | A1 | 6/2017 | Scheunemann et al. |
| 2017/0319453 | A1* | 11/2017 | Ando ..................... A61K 8/466 |
| 2017/0367962 | A1* | 12/2017 | Bentley ................. A61K 8/8152 |
| 2018/0015009 | A1 | 1/2018 | Soubiran et al. |
| 2018/0071198 | A1 | 3/2018 | Lin et al. |

FOREIGN PATENT DOCUMENTS

| | | |
|---|---|---|
| CN | 102639108 | 8/2012 |
| CN | 102821745 | 12/2012 |
| CN | 103458858 | 12/2013 |
| CN | 104487139 | 4/2015 |
| CN | 105163808 | 12/2015 |
| EP | 0530974 | 3/1993 |
| EP | 3481363 | 4/2020 |
| JP | 2009227659 | 10/2009 |
| JP | 2014076983 A | 5/2014 |
| JP | 2015027977 A | 2/2015 |
| RU | 2230473 C2 | 6/2004 |
| RU | 2619209 C2 | 5/2017 |
| WO | WO9631188 | 10/1996 |
| WO | WO2007065537 | 6/2007 |
| WO | WO2008037609 | 4/2008 |
| WO | WO2011003068 | 1/2011 |
| WO | WO2012110387 | 8/2012 |
| WO | WO2012138696 | 10/2012 |
| WO | WO2013122861 | 8/2013 |
| WO | 2014046300 A2 | 3/2014 |
| WO | WO2015082241 | 6/2015 |
| WO | WO2016085707 | 6/2016 |
| WO | WO2017001385 | 1/2017 |
| WO | WO2017071915 | 5/2017 |
| WO | WO2018007332 | 1/2018 |
| WO | WO-2018007332 A1 * | 1/2018 ............. A61K 8/064 |
| WO | 2019121428 A1 | 6/2019 |
| WO | WO2020254320 | 12/2020 |

OTHER PUBLICATIONS

Search Report and Written Opinion in PCTEP2018075450; Oct. 25, 2018; World Intellectual Property Org. (WIPO).
Search Report and Written Opinion in PCTEP2018085074; Jan. 29, 2019; World Intellectual Property Org. (WIPO).
Search Report in EP19181766; Jan. 15, 2020; European Patent Office (EPO).
Search Report in EP19178752; Dec. 4, 2019; European Patent Office (EPO).
Anonymous; Database GNPD [online]; Damage Repair Shampoo XP055642900; Mar. 26, 2015; database accession No. 3068005.
Brenntag Specialties, Inc.; Formularies; Hair Care Kits CASCC Suppliers Day 2015; May 1, 2015; retrieved from internet; retrieved on Nov. 15, 2019; BSI Cosmetic Ingredients.
Search Report and Written Opinoin in EP19181752; Jan. 9, 2020; European Patent Office (EPO).
Written Opinion in EP16178241; Sep. 16, 2016; European Patent Office (EPO).
IPRP1 in PCTEP2017066523; Jan. 8, 2019; World Intellectual Property Org. (WIPO).
Written Opinion in EP19178752; Dec. 4, 2019; European Patent Office (EPO).
Search Report and Written Opinion in PCTEP2020065443; Aug. 17, 2020; World Intellectual Property Org. (WIPO).
Written Opinion in EP19181766; Jan. 15, 2020; European Patent Office (EPO).
Search Report and Written Opinion in PCTEP2020066615; Sep. 8, 2020; World Intellectual Property Org. (WIPO).
Opposition Notice in EP17737763 (EP3481363); Jan. 18, 2021; European Patent Office (EPO).
GNPD Mintel; Redensifying Repairing Shampoo; Sensilis Densage; Jul. 2016; pp. 1-2, Record ID 4122655; Spain.
Dave Popplewell; N-DurHance A-1000 polymer; Ashland; pp. 1-17.
Popplewell and Nuutinen; New ingredient for conditioning cleansing systems; Ashland; Nov. 24, 2014; pp. 1-6, www.manufacturingchemist.com.
Search Report and Written Opinion in PCTEP2020066619; Sep. 8, 2020.
Search Report and Written Opinion in PCTEP2020066615; Sep. 8, 2020.

* cited by examiner

CLEANSING COMPOSITION

CROSS REFERENCE TO RELATED APPLICATIONS

The present application is a U.S. National Phase Application under 35 U.S.C. § 371 of International Application No. PCT/EP2020/066615, filed on Jun. 16, 2020, which claims priority to European patent application No. 19181766.7 filed on Jun. 21, 2019, the contents of which are incorporated herein in their entireties.

FIELD OF THE INVENTION

The present invention relates to mild sulphate free cleansing compositions for hair and scalp.

BACKGROUND AND PRIOR ART

US 2012/276210 relates to shampoo compositions containing polyacrylate microcapsules, wherein the polyacrylate microcapsules have increased deposition onto hair. A shampoo composition is disclosed comprising:
 (a) from about 0.001% to about 10% of an anionic charged polyacrylate microcapsule;
 (b) from about 0.01% to about 2% of a cationic deposition polymer; and
 (c) from about 2% to about 25% of a detersive surfactant; and
 (d) a carrier.

WO 2007/065537 addresses a problem associated with the use of cationic deposition polymers in that it is difficult to obtain a good balance of conditioning benefits at different stages of the shampooing process, and discloses an aqueous shampoo composition comprising:
 (i) one or more anionic cleansing surfactants;
 (ii) discrete, dispersed droplets of a water-insoluble conditioning agent with a mean droplet diameter (D3,2) of 4 micrometres or less;
 (iii) one or more cationic polymers (A) selected from cationically modified acrylamide polymers having a cationic charge density at pH7 of less than 1.0 meq per gram, cationically modified celluloses and mixtures thereof, and
 (iv) one or more cationic polymers (B) selected from cationically modified acrylamide polymers having a cationic charge density at pH7 of greater than 1.0 meq per gram, cationically modified polygalactomannans, and mixtures thereof, wherein the composition comprises a cationic polymer other than a cationically modified acrylamide polymer.

WO 2013/122861 discloses a conditioning composition additive for providing immediate and prolonged benefit to a keratin surface comprising:
 a) a hydrophobically modified poly(acrylamido-N-propyltrimethylammonium chloride) (polyAPTAC) and b) water;
 wherein the hydrophobically modified polyAPTAC is present in an amount of from 0.1 wt % to 20 wt % of the total weight of the conditioning composition additive and has a cationic charge density in the range of about 1 to 8 meq/g.

US2012/0076747 discloses a surfactant-based cleansing composition comprising, a surfactant, cationic, water-soluble polyelectrolytes and the use of the composition in personal care and household care cleansing compositions for treating keratinous substrates, textile substance and hard-surface substrates.

US2018/015009 discloses a microcapsule and a copolymer of acrylamide and acrylamidopropyltrimonium chloride as a first deposition aid to facilitate the deposition of the microcapsule onto a hard surface such as skin, hair, fabric and floor.

WO2018/007332 discloses personal cleansing composition comprising: (i) an aqueous continuous phase including cleansing surfactant; (ii) one or more oily liquid conditioning agents for skin and/or hair wherein the agent is solubilized in wormlike micelles in the aqueous continuous phase via the incorporation of at least one inorganic electrolyte and at least one linker molecule; (iii) one or more cationic deposition polymers which are selected from cationic polygalactomannans having a mean charge density at pH7 from 0.2 to 2 meq per gram; and (iv) a hair substantive cationic conditioning polymer which is a homopolymer of (3-acrylamidopropyl) trimethyl ammonium chloride.

Many cleansing and conditioning products for use on hair contain silicones. It is desirable to deposit silicone onto hair in order to confer conditioning and sensory benefits. A typical hair wash process involves first washing hair with a shampoo and rinsing, followed by applying a conditioner product and rinsing.

Silicone can be deposited onto hair from a shampoo.

However, we have found that this silicone is largely deterged when the hair is subsequently washed with a conditioner as part of a typical washing process. A consequence of this is that it is necessary to include silicone in the conditioner in order to provide conditioning benefits that are apparent when the hair has dried.

We have now found that a shampoo comprising a conditioning polymer which is an APTAC polymer, preferably selected from a homopolymer of (3-acrylamidopropyl) trimethyl ammonium chloride and a (3-acrylamidopropyl) trimethyl ammonium chloride/acrylamide copolymer can enhance the adhesion of the silicone delivered from shampoo and help retain it on hair during and after washing with a conditioner.

When the hair is washed with a shampoo containing a conditioning polymer which is an APTAC polymer, preferably selected from a homopolymer of (3-acrylamidopropyl) trimethyl ammonium chloride and a (3-acrylamidopropyl) trimethyl ammonium chloride/acrylamide copolymer and then a silicone free conditioner, it has a significantly higher disposition of silicone compared to hair that is washed with a 1% silicone containing shampoo and then a silicone free conditioner.

In dry friction data, the hair that is washed with a shampoo containing which is an APTAC polymer, preferably selected from a homopolymer of (3-acrylamidopropyl) trimethyl ammonium chloride and a (3-acrylamidopropyl) trimethyl ammonium chloride/acrylamide copolymer and then a silicone free conditioner has a significantly lower dry friction compared to the hair that is washed with a 1% silicone containing shampoo and then a silicone free conditioner.

Addition of silicone to a shampoo formulation is known to have a detrimental effect on the foaming properties, for example flash foam and foam height.

The inventors have identified Alpha Olefin Sulfonate (AOS) as a sulfate free, primary surfactant. As with sulfate based chassis a secondary surfactant is required to help build viscosity using salt, control the foam and aid in the delivery of mildness benefits through lower CMC.

It is desirable to reduce the level of surfactant used in formulations (for mildness and environmental benefits). We have found that if you reduce the amount of surfactant, then the viscosity of the formulation falls undesirably.

However, the typical secondary surfactant, cocamidopropyl betaine (CAPB) does not allow viscosity to be built at low total surfactant concentrations with Alpha Olefin Sulfonate (AOS) as the primary surfactant.

The inventors have now found that a combination of AOS, at a specified ratio, with at least one of an alkyl betaine, an alkyl hydroxy sultaine, an alkyl aminopropyl hydroxy sultaine or an alkyl amphoacetate can afford viscosity builds with salt addition at low total concentrations of surfactant. This negates the need for other thickening agents, for example, polymers and other secondary surfactants.

Use of such APTAC polymers in a shampoo composition having a combination of anionic and amphoteric sulfate free surfactants at enriched amphoteric ratios; reduced surfactant concentrations; specific primary sulfate free surfactant levels, a cationic conditioning polymer and a silicone emulsion to provide good foamability, dry lubrication that provides silky, smooth feel and desirable rheological characteristics, whilst maintaining mildness to skin and hair protein as well as increased silicone delivery and retention.

SUMMARY OF THE INVENTION

In a first aspect the present invention provides an aqueous, sulphate free shampoo for hair and scalp comprising:—
a. a pre-formed emulsified silicone;
b. a cationic deposition polymer;
c. a hair substantive cationic conditioning polymer which is an APTAC polymer having a molecular weight of less than 1 million Daltons, preferably selected from a homopolymer of (3-acrylamidopropyl) trimethyl ammonium chloride and a (3-acrylamidopropyl) trimethyl ammonium chloride/acrylamide copolymer;
d. a total amount of anionic surfactant, amphoteric surfactant and zwitterionic surfactant consisting of:
   (i) from 3 wt % to 13 wt %, by weight of the total composition at 100% activity, of an alpha olefin sulfonate anionic surfactant of general formula (I):

   (I)

in which $R^1$ is selected from linear or branched alkyl groups having from 11 to 13 carbon atoms and mixtures thereof; and M is a solubilizing cation;
   (ii) from 1 to 6%, by weight of an amphoteric or zwitterionic surfactant, selected from an alkyl betaine of general formula (II)

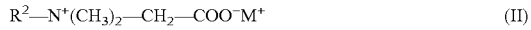   (II)

wherein $R^2$=C12 (Lauryl) or Coco derived;
   an alkyl hydroxy sultaine of general formula (III),

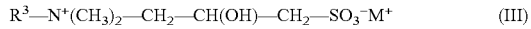   (III)

wherein $R^3$=C12 (Lauryl) or Coco derived;
   an alkyl aminopropyl hydroxy sultaine of general formula (IV),

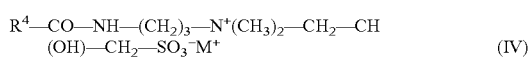   (IV)

wherein $R^4$=C12 (Lauryl) or Coco derived;
   an alkyl amphoacetate of general formula (V),

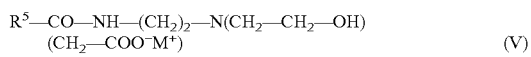   (V)

wherein $R^5$=C12 (Lauryl) or Coco derived;
   and mixtures thereof; and
e. a suspending agent in which the weight ratio of (i) to (ii) ranges from 1:1 to 6:1 and the pH of the composition is from 3 to 6.5
and wherein the composition has a viscosity from 3,500 to 15,000 mPa·s, preferably from 4,000 to 12,000 mPa·s when measured using a Brookfield V2 viscometer using a spindle RTV5, for 1 minute at 20 rpm at 30° C.

In a second aspect, the present invention provides a method of treating hair comprising the steps of applying to hair the composition of the first aspect and performing a first rinse with water.

Silicone is deposited onto the hair from the composition of the invention, during the method of the invention.

Preferably, the method comprises a subsequent steps of applying a conditioner composition and then performing a second rinse with water. Following these subsequent steps, the silicone that is deposited on the hair from the composition of the invention remains on the hair.

Some or all of the silicone is retained on the hair following rinse with water, and/or following treatment with a hair conditioner and a second rinse. By "retained" on the hair is meant that the silicone remains on the hair.

DETAILED DESCRIPTION AND PREFERRED EMBODIMENTS

The Emulsified Silicone

The composition of the invention comprises a pre-formed emulsified silicone. Mixtures of emulsified silicones can be used.

Suitable silicones include polydiorganosiloxanes, in particular polydimethylsiloxanes which have the CTFA designation dimethicone. Also suitable for use compositions of the invention are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the compositions of the invention will typically have a D90 silicone droplet size in the composition of less than 30, preferably less than 20, more preferably less than 10 micron, ideally from 0.01 to 1 micron. Silicone emulsions having an average silicone droplet size (D50) of 0.15 micron are generally termed microemulsions.

Silicone particle size may be measured by means of a laser light scattering technique, for example using a 2600D Particle Sizer from Malvern Instruments.

Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of emulsified silicones for inclusion in compositions of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone".

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

Preferably, the silicone is selected from the group consisting of dimethicone, dimethiconol, amodimethicone and mixtures thereof. Also preferred are blends of amino-functionalised silicones with dimethicones.

The amount of silicone in compositions of the invention may suitably range from 0.05 to 10%, preferably from 0.1 to 8%, more preferably 0.5 to 6.5%, most preferably 1 to 3% at 100% activity, based on the total weight of the composition.

The Cationic Deposition Polymer

The composition of the invention includes a cationic deposition polymers which may be selected from cationic polygalactomannans having a mean charge density at pH7 from 0.2 to 2 meq per gram. Such polymers may serve to enhance the delivery of conditioning agents from the composition to the skin and/or hair surface during consumer use, thereby improving the conditioning benefits obtained. Mixtures of cationic deposition polymers may be employed.

The term "charge density" in the context of this invention refers to the ratio of the number of positive charges on a monomeric unit of which a polymer is comprised to the molecular weight of the monomeric unit. The charge density multiplied by the polymer molecular weight determines the number of positively charged sites on a given polymer chain. The polygalactomannans are polysaccharides composed principally of galactose and mannose units and are usually found in the endosperm of leguminous seeds, such as guar, locust bean, honey locust, flame tree, and the like. Guar flour is composed mostly of a galactomannan which is essentially a straight chain mannan with single membered galactose branches. The mannose units are linked in a 1-4-β-glycosidic linkage and the galactose branching takes place by means of a 1-6 linkage on alternate mannose units. The ratio of galactose to mannose in the guar polymer is therefore one to two.

Suitable cationic polygalactomannans for use in the invention include polygalactomannans, such as guars, and polygalactomannan derivatives, such as hydroxyalkyl guars (for example hydroxyethyl guars or hydroxypropyl guars), that have been cationically modified by chemical reaction with one or more derivatizing agents.

Derivatizing agents typically contain a reactive functional group, such as an epoxy group, a halide group, an ester group, an anhydride group or an ethylenically unsaturated group, and at least one cationic group such as a cationic nitrogen group, more typically a quaternary ammonium group. The derivatization reaction typically introduces lateral cationic groups on the polygalactomannan backbone, generally linked via ether bonds in which the oxygen atom corresponds to hydroxyl groups on the polygalactomannan backbone which have reacted.

Preferred cationic polygalactomannans for use in the invention include guar hydroxypropyltrimethylammonium chlorides.

Guar hydroxypropyltrimethylammonium chlorides for use in the invention are generally comprised of a nonionic guar gum backbone that is functionalized with ether-linked 2-hydroxypropyltrimethylammonium chloride groups, and are typically prepared by the reaction of guar gum with N-(3-chloro-2-hydroxypropyl) trimethylammonium chloride.

Cationic polygalactomannans for use in the invention (preferably guar hydroxypropyltrimethylammonium chlorides) generally have an average molecular weight (weight average molecular mass (Mw) determined by size exclusion chromatography) in the range 500,000 to 3 million g/mol, more preferably 800,000 to 2.5 million g/mol.

Cationic polygalactomannans for use in the invention generally have a charge density ranging from 0.5 to 1.8 meq/g.

Preferably the cationic polygalactomannans are selected from guar hydroxypropyltrimethylammonium chlorides having a charge density ranging from 0.5 to 1.8 meq/g (and mixtures thereof).

The cationic charge density of the polymer is suitably determined via the Kjeldahl method as described in the US Pharmacopoeia under chemical tests for nitrogen determination.

Specific examples of preferred cationic polygalactomannans are guar hydroxypropyltrimonium chlorides having a cationic charge density from 0.5 to 1.1 meq/g.

Also suitable are mixtures of cationic polygalactomannans in which one has a cationic charge density from 0.5 to 1.1 meq/g, and one has a cationic charge density from 1.1 to 1.8 meq per gram.

Specific examples of preferred mixtures of cationic polygalactomannans are mixtures of guar hydroxypropyltrimonium chlorides in which one has a cationic charge density from 0.5 to 1.1 meq/g, and one has a cationic charge density from 1.1 to 1.8 meq per gram.

Cationic polygalactomannans for use in the invention are commercially available from Solvay as JAGUAR® C13S, JAGUAR® C14 and JAGUAR® C17. Also Esaflor 0X 14B from Lamberti.

In a preferred composition according to the invention the cationic polygalactomannans are selected from guar hydroxypropyltrimethylammonium chlorides having a charge density ranging from 0.5 to 1.8 meq/g (and mixtures thereof), at a level ranging from 0.15 to 0.2% by weight based on the total weight of the composition.

The cationic deposition polymer is preferably present in an amount of from 0.05 to 1 wt %, preferably from 0.1 to 0.5 wt %, most preferably from 0.15 to 0.2 wt % based on the total weight of the composition.

The Hair Substantive Cationic Conditioning Polymer

The composition of the invention includes a hair substantive cationic conditioning polymer which is an APTAC polymer having a molecular weight of less than 1 million Daltons, preferably selected from a homopolymer of (3-acrylamidopropyl) trimethyl ammonium chloride and a (3-acrylamidopropyl) trimethyl ammonium chloride/acrylamide copolymer.

WO2013/122861 describes the synthesis of (3-acrylamidopropyl) trimethyl ammonium chloride (APTAC) homopolymers of varying molecular weights, using a radical polymerisation reaction. According to the described method, APTAC monomer is polymerised in an aqueous medium by a discontinuous adiabatic process using an azo or persulfate radical initiator. The APTAC homopolymers so obtained have molecular weights ranging from about 100,000 g/mol to about 1,000,000 g/mol. The molecular weight can be determined by using standard analytical measurements, such as size exclusion chromatography (SEC).

A polymer suitable for use in the invention is commercially available from Ashland, Inc. as N-DurHance™ A-1000 Conditioning Polymer (supplied as a 20% a.i. aqueous solution of the polymer). A suitable copolymer of (3-acrylamidopropyl) trimethyl ammonium chloride/acrylamide copolymer is available from Ashland as N-DurHance AA2000.

The APTAC polymer for use in the invention, preferably has a charge density at pH 7 of greater than 3, most preferably from 4 to 6.

The APTAC polymer for use in the invention has a molecular weight of less than 1 million Daltons, more preferably 100,000 to 950,000 Daltons, most preferably from 200,000 to 900,000 Daltons.

In a preferred embodiment the APTAC polymer has a charge density at pH 7 of from 4 to 6. and a molecular weight of 100,000 to 950,000 Daltons.

Suitable methods of measuring charge density and molecular weight are as given above.

In a typical composition according to the invention the level of polymer (per se as active ingredient) generally ranges from 0.05 to 5%, more preferably from 0.1 to 2%, most preferably from 0.15 to 1% (by weight based on the total weight of the composition).

Preferably the composition comprises an isotropic surfactant phase, where under dilution, isotropic micelles provide higher availability of monomers to the air/water interface, whereas anisotropic may diffuse at a slower rate, resulting in lower flash foam properties. Thus, the isotropic phase is advantageous for product appearance, clarity and good flash foam properties.

The Surfactants

All amounts referred to herein are based on 100% activity (or "active") unless otherwise stated. By 100% activity (or "active") is meant that the material is not diluted and is at 100% v/v or wt/wt. Many materials used in personal care formulations are commercially available at different active concentrations, for example at 70% active or 60% active. For example, 100 ml of 70% active surfactant provides the same amount of active material as 70 ml of 100% active surfactant. Therefore, in order to provide for variations in activities of materials, all amounts are based on 100% active materials.

The composition comprises a total amount of anionic, amphoteric and zwitterionic surfactant consisting of (i) and (ii) below. That is to say, no further anionic, amphoteric and zwitterionic surfactants are present in the compositions of the invention. Preferably, no other surfactants, for example, nonionic surfactants are present in the compositions of the invention.

(i) The Alpha Olefin Sulfonate Anionic Surfactant

The composition of the invention comprises (i) one or more alpha olefin sulfonate anionic surfactants of general formula (I)

in which $R^1$ is selected from linear or branched alkyl groups having from 11 to 13 carbon atoms and mixtures thereof; and M is a solubilizing cation;

Preferably $R^1$ in general formula (I) is a $C_{14}$ or $C_{16}$ linear alkyl group.

Preferably M in general formula (I) is selected from alkali metal cations (such as sodium or potassium), ammonium cations and substituted ammonium cations (such as alkylammonium, alkanolammonium or glucammonium).

Commercially produced alpha olefin sulfonate anionic surfactants of general formula (I) may be made by sulfating C14-16 olefins derived from natural gas. The process can also yield mixtures of homologues and low levels of unreacted olefins.

Particularly preferred is alpha olefin sulfonate with an average of 14-16 carbons. A suitable example of such a material is Bioterge AS40 (ex Stepan).

The amount of alpha olefin sulfonate anionic surfactant, at 100% activity, of general formula (I) ranges from 3 to 13%, for example from 3 to 12.85%, preferably from 3.5 to 12%, more preferably from 3 to 10%, still more preferably from 3 to 9% and most preferably from 3.25 to 8% (by weight based on the total weight of the composition).

(ii) The Amophoteric or Zwitterionic Surfactant of General Formulae (II), (III), (IV) or (V)

The composition of the invention comprises (ii) an amphoteric or zwitterionic surfactant, selected from an alkyl betaine of general formula (II)

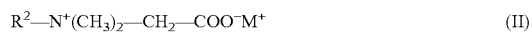

wherein $R^2$=C12 (Lauryl) or Coco derived;
an alkyl hydroxy sultaine of general formula (III),

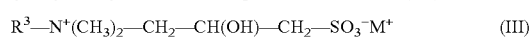

wherein $R^3$=C12 (Lauryl) or Coco derived;
an alkyl aminopropyl hydroxy sultaine of general formula (IV),

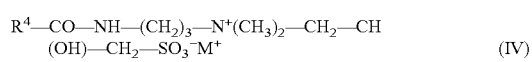

wherein $R^4$=C12 (Lauryl) or Coco derived;
an alkyl amphoacetate of general formula (V),

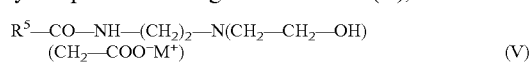

wherein $R^5$=C12 (Lauryl) or Coco derived;
and mixtures thereof.

The preferred surfactant (ii) is selected from coco betaine, lauryl hydroxy sultaine, coco aminopropyl hydroxy sultaine, lauryl amphoacetate and mixtures thereof, most preferably selected from coco betaine, lauryl hydroxy sultaine and mixtures thereof.

The amount of amphoteric or zwitterionic surfactants of general formula (II), (III), (IV) or (V) or mixtures thereof, preferably ranges from 1 to 6%, more preferably from 1 to 5%, most preferably from 1.2 to 4% (based on the total weight of the composition and 100% activity).

In a preferred composition according to the invention the amphoteric or zwitterionic surfactant (ii) is selected from coco betaine, lauryl hydroxy sultaine, coco aminopropyl hydroxy sultaine, lauryl amphoacetate and mixtures thereof, in an amount ranging from 1 to 4% (by weight based on the total weight of the composition and 100% activity).

In a more preferred composition the amphoteric or zwitterionic surfactant (ii) is selected from a betaine amphoteric surfactant of general formula (II), which is coco betaine, an amphoteric surfactant of general formula (III), which is lauryl hydroxy sultaine, and mixtures thereof, in an amount of from 1 to 4% (by weight based on the total weight of the composition and 100% activity).

An especially preferred composition according to the invention comprises (i) alpha olefin sulfonate in an amount ranging from 3.25 to 8% (by weight based on the total weight of the composition and 100% active material); and (ii) an amphoteric or zwitterionic surfactant selected from coco betaine, lauryl hydroxy sultaine, coco aminopropyl hydroxy sultaine, lauryl amphoacetate or mixtures thereof, in an amount ranging from 1 to 4% (by weight based on the total weight of the composition and 100% active material).

The combined amount of (i) and (ii) ranges from 4 to 19 wt %, preferably from 5 to 15 wt %, most preferably from 5 to 11 wt % (based on the total weight of the composition and 100% activity).

The weight ratio of the alpha olefin sulfonate anionic surfactant (i) to the amphoteric surfactant (ii) ranges from 1:1 to 6:1, preferably from 1.5:1 to 4.5:1 and most preferably 2:1 to 4:1.

The pH of the composition of the invention ranges from 3 to 6.5, preferably from 3.5 to 5.1, more preferably from 4 to 5.

A protonating agent may be used for achieving the low pH. Suitable protonating agents are acids. Suitable acids useful herein include hydrochloric acid, citric acid, acetic acid, tartaric acid, fumaric acid, lactic acid, malic acid, succinic acid, and mixtures thereof. Preferably, the acid is selected from the group consisting of citric acid, acetic acid, tartaric acid, hydrochloric acid, fumaric acid, lactic acid and mixtures thereof.

The Suspending Agent

The composition of the invention includes one or more suspending agents. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives, since these impart pearlescence to the composition. Polyacrylic acid is available commercially as Carbopol 420, Carbopol 488 or Carbopol 493. Polymers of acrylic acid cross-linked with a polyfunctional agent may also be used; they are available commercially as Carbopol 910, Carbopol 934, Carbopol 941 and Carbopol 980. An example of a suitable copolymer of a carboxylic acid containing monomer and acrylic acid esters is Carbopol 1342. All Carbopol (trademark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Mixtures of any of the above suspending agents may be used. Preferred is a mixture of cross-linked polymer of acrylic acid and crystalline long chain acyl derivative. The suspending agent will generally be present in a shampoo composition for use in the invention at levels of from 0.1 to 10%, preferably from 0.15 to 6%, more preferably from 0.2 to 4% by total weight of suspending agent based on the total weight of the composition Water The aqueous composition of the invention preferably comprises from about 50 to about 90%, preferably from about 55 to about 85%, more preferably from about 60 to about 85%, most preferably from about 65 to about 83% water (by weight based on the total weight of the composition).

The Inorganic Electrolyte

We have found that, surprisingly, the compositions of the invention are amenable to building viscosity very well. It is thus possible to build viscosity at lower concentrations at enriched surfactant ratios. This is further advantage of the invention.

The composition of the invention preferably includes at least one inorganic electrolyte. The inorganic electrolyte provides viscosity to the composition.

The viscosity of the composition ranges from 2,500 to 25,000 mPa·s, preferably from 3,000 to 20,000 mPa·s, more preferably from 3,500 to 15,000 mPa·s, most preferably from 4,000 to 12,000 mPa·s when measured using a Brookfield V2 viscometer (spindle RTV5, 1 minute, 20 rpm) at 30° C.

At these ranges our products are pourable yet thick enough to satisfy the consumer desire for thick compositions.

Suitable inorganic electrolytes include metal chlorides (such as sodium chloride, potassium chloride, calcium chloride, magnesium chloride, zinc chloride, ferric chloride and aluminium chloride) and metal sulfates (such as sodium sulfate and magnesium sulfate).

It is intended that the inorganic electrolyte is separate from any inorganic electrolytes that may be present in the raw materials of the invention.

Examples of preferred inorganic electrolytes for use in the invention include sodium chloride, potassium chloride, magnesium sulfate and mixtures thereof.

Mixtures of any of the above described materials may also be suitable.

The amount of inorganic electrolyte in compositions of the invention preferably ranges from 0.5 to 10%, more preferably from 0.75 to 7%, even more preferably from 1 to 5% and most preferably from 1 to 3% (by weight based on the total weight of the composition).

A preferred composition of the invention has a weight ratio of (i) an alpha olefin sulfonate anionic surfactant of general formula (I) to (ii) an amphoteric or zwitterionic surfactant of general formula (II), (III), (IV), (V) or mixtures thereof, of from 2:1 to 4:1 and comprises an amount of inorganic electrolyte of from 1 to 3 wt % based on total weight of the composition.

A further preferred composition of the invention has a weight ratio of (i) an alpha olefin sulfonate anionic surfactant of general formula (I) to (ii) an amphoteric or zwitterionic surfactant of general formula (II), (III), (IV), (V) or mixtures thereof, of from greater than 4:1 to 6:1, preferably 5:1 to 6:1 and comprises an amount of inorganic electrolyte of from 1 to 5, preferably from greater than 3 to 5 wt %, more preferably 4 to 5 wt % based on total weight of the composition.

Preferably, the compositions of the invention are free from thickening agents selected from thickening polymers and secondary surfactants not included in (ii). In the context of the invention, by free from is meant having less than 0.4 weight %, more preferably less than 0.1 weight %, even more preferably less than 0.05 weight %, still more preferably less than 0.001 weight %, yet preferably less than 0.0001 weight %, and most preferably 0 weight % of thickening agents by weight of the total composition. For the sake of clarity, the cationic polymer (iii) of the invention is not intended to be a thickening polymer.

A Preservative

The composition of the invention preferably comprises one or more preservatives, selected from sodium benzoate, sodium salicylate, benzyl alcohol, phenoxyethanol, 1,2-alkanediols, Iodopropynyl butylcarbamate (IPBC), 5-chloro-2-methyl-2H-isothiazol-3-one, 2-methyl-2H-isothiazol-3-one, or mixtures thereof. Preferably the preservative is an organic acid, most preferably the preservative is sodium benzoate.

A preferred composition has a pH of from 3 to 5.8, preferably 4 to 5 and comprises a preservative that is sodium benzoate.

Other Ingredients

Preferably, the composition of the invention further comprises one or more structurants to assist in the suspension of dispersed benefit agent and provide phase stability. Suitable structurants include polyacrylic acids, polymethacrylic acids, cross-linked polymers of acrylic acid, cross-linked polymers of methacrylic acid, copolymers of acrylic acid with a hydrophobic monomer, copolymers of methacrylic acid with a hydrophobic monomer, copolymers of carboxylic acid-containing monomers and acrylic esters, copolymers of carboxylic acid-containing monomers and methacrylic esters, cross-linked copolymers of acrylic acid and acrylate esters, cross-linked copolymers of methacrylic acid and acrylate esters heteropolysaccharide gums and crystalline long chain acyl derivatives.

Preferred structurants are selected from polyacrylic acids, polymethacrylic acids, cross-linked polymers of acrylic acid, cross-linked polymers of methacrylic acid and mixtures thereof.

Mixtures of any of the above structurants may be used.

When included, the total amount of structurant is generally 0.1 to 10%, preferably from 0.1 to 3%, more preferably from 0.2 to 2%, most preferably from 0.3 to 0.9% (by weight based on the total weight of the composition).

A preferred composition comprises a structurant selected from polyacrylic acids, polymethacrylic acids, cross-linked polymers of acrylic acid, cross-linked polymers of methacrylic acid and mixtures thereof in an amount of from 0.1 to 10%, preferably from 0.1 to 3%, more preferably from 0.2 to 2%, most preferably from 0.3 to 0.9% (by weight based on the total weight of the composition).

A composition of the invention may contain further optional ingredients to enhance performance and/or consumer acceptability. Examples of such ingredients include fragrance, dyes and pigments. Each of these ingredients will be present in an amount effective to accomplish its purpose. Generally, these optional ingredients are included individually at an amount of up to 5% (by weight based on the total weight of the composition).

The composition of the invention is primarily intended for topical application to the hair and scalp.

Most preferably the composition of the invention is topically applied to the hair and then massaged into the hair and scalp. The composition is then rinsed off the hair and scalp with water prior to drying the hair.

The invention will be further illustrated by the following, non-limiting Examples.

EXAMPLES

Example 1: Preparation of Compositions 1 to 2 in Accordance with the Invention Rinse-off aqueous hair cleansing shampoo formulations may be prepared, having ingredients as shown in Table 1 below.

The shampoos may suitably be prepared using the following method:

1. A vessel was charged with water. Surfactants and any structurant were added with stirring.
2. The mixture was heated to 30° C. and mixed until completely homogenous.
3. The silicone emulsion was then added and mixed well.
4. The Acrylamidopropyltrimonium Chloride/Acrylamide Copolymer was then added and mixed well.
5. The pH was adjusted to pH 4.5 using citric acid.

TABLE 1

Compositions 1 and 2 in accordance with the invention

| INCI and/or Trade Name | % active | 1 | 2 |
|---|---|---|---|
| Alpha Olefin Sulfonate (Bioterge AS-40) | 38.5 | 19.09 | 19.09 |
| Coco betaine/Genagen KB | 30 | 8.83 | — |
| Lauryl Hydroxy Sultaine/Mackam LHS E | 50 | — | 5.30 |
| Acrylamidopropyltrimonium Chloride/Acrylamide Copolymer[1] | 20 | 1 | 1 |
| Guar Hydroxypropyltrimonium Chloride | 100 | 0.185 | 0.185 |
| Citric acid | 100 | to pH 4.5 | to pH 4.5 |
| Carbomer | 100 | 0.3 | 0.3 |
| Perfume | 100 | 0.5 | 0.5 |
| Dimethiconol/TEA-dodecylbenzene sulfonate | 50 | 3 | 3 |
| Water | to 100 | to 100% | to 100% |

[1]N-DurHance ™ AA2000 ex Ashland

The invention claimed is:

1. An aqueous, sulphate free shampoo composition for hair and scalp comprising:
   a. a pre-formed emulsified silicone;
   b. a cationic deposition polymer;
   c. a hair substantive cationic conditioning polymer which is an APTAC polymer having a molecular weight of less than 1 million Daltons, a charge density at pH 7 above 4, and is a homopolymer of (3-acrylamidopropyl) trimethyl ammonium chloride;
   d. a total amount of anionic surfactant, amphoteric surfactant and zwitterionic surfactant consisting of:
   (i) from 3 wt % to 13 wt %, by weight of the total composition at 100% activity, of an alpha olefin sulfonate anionic surfactant of general formula (I):

$$R^1-CH=CH-CH_2-SO_3^-M^+ \quad (I)$$

in which $R^1$ is selected from linear or branched alkyl groups having from 11 to 13 carbon atoms and mixtures thereof; and M is a solubilizing cation;
   (ii) from 1 to 6%, by weight of an amphoteric or zwitterionic surfactant, selected from an alkyl betaine of general formula (II)

$$R^2-N+(CH_3)_2-CH_2-COO^-M^+ \quad (II)$$

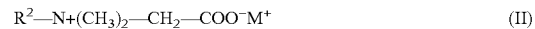

wherein $R^2$=C12 (Lauryl) or Coco derived;
   an alkyl hydroxy sultaine of general formula (III), $$R^3-N^+(CH_3)_2-CH_2-CH(OH)-CH_2-SO_3^-M^+ \quad (III)$$

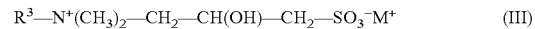

wherein $R^3$=C12 (Lauryl) or Coco derived;
   an alkyl aminopropyl hydroxy sultaine of general formula (IV), $$R^4-CO-NH-(CH_2)3-N^+(CH_3)_2-CH_2-CH(OH)-CH_2-SO_3^-M^+ \quad (IV)$$

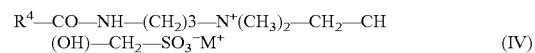

wherein $R^4$=C12 (Lauryl) or Coco derived;
   an alkyl amphoacetate of general formula (V), $$R^5-CO-NH-(CH_2)_2-N(CH_2-CH_2-OH)(CH_2-COO^-M^+) \quad (V)$$

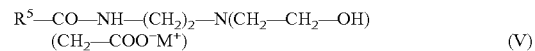

wherein R⁵=C12 (Lauryl) or Coco derived;
and mixtures thereof; and e. a suspending agent in which the weight ratio of (i) to (ii) ranges from 1:1 to 6:1 and the pH of the composition is from 3 to 6.5;

and wherein the composition has a viscosity from 3,500 to 15,000 mPa·s when measured using a Brookfield V2 viscometer using a spindle RTV5 for 1 minute at 20 rpm at 30° C.

2. The composition of claim 1, wherein the amount of emulsified silicone is from 0.01 to 10 wt % based on the total weight of the composition and 100% activity.

3. The composition according to claim 1, wherein the amount of alpha olefin sulfonate anionic surfactant of general formula (I) is from 3 to 12.85%, by weight based on the total weight of the composition and at 100% activity.

4. The composition according to claim 1, wherein the amount of amphoteric or zwitterionic surfactants of general formula (II), (III), (IV) or (V) is from 1 to 4% based on the total weight of the composition and 100% activity.

5. The composition according to claim 1, in which the combined amount of (i) and (ii) ranges from 5 wt % to 15 wt % by weight based on the total weight of the composition.

6. The composition according to claim 1, wherein the weight ratio of the alpha olefin sulfonate anionic surfactant (i) to the amphoteric or zwitterionic surfactant (ii) is from 1.5:1 to 4.5:1.

7. The composition according to claim 1, wherein the amphoteric or zwitterionic surfactant (ii) is selected from a betaine amphoteric surfactant of general formula (II), which is coco betaine, an amphoteric surfactant of general formula (III), which is lauryl hydroxy sultaine, and mixtures thereof, in an amount of from 1 to 4% by weight based on the total weight of the composition and 100% activity.

8. The composition according to claim 1, in which the cationic deposition polymer is a cationic polygalactomannan selected from guar hydroxypropyltrimethylammonium chlorides with a charge density ranging from 0.5 to 1.8 meq/g and mixtures thereof.

9. The composition according to claim 8, in which the level of the guar hydroxypropyltrimethylammonium chloride(s) ranges from 0.15 to 0.2% by weight based on the total weight of the composition.

10. The composition according to claim 1, wherein the suspending agent is selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and long chain acyl derivatives.

11. The composition according to claim 1, wherein the suspending agent is present at levels of from 0.1 to 10 wt % by total weight of suspending agent based on the total weight of the composition.

12. The composition according to claim 1, wherein the APTAC polymer has a molecular weight of 100,000 to 950,000 Daltons.

13. The composition according to claim 1, wherein the composition is free from thickening agents selected from thickening polymers and secondary surfactants not defined in (ii).

14. The composition according to claim 1, further comprising an inorganic electrolyte, and wherein the weight ratio of (i) to (ii) is from 2:1 to 4:1.

15. The composition according to claim 1, wherein the composition has a viscosity 4,000 to 12,000 mPa·s.

16. The composition according to claim 1, wherein the amount of alpha olefin sulfonate anionic surfactant of general formula (I) is from 3.5 to 12% by weight based on the total weight of the composition and at 100% activity.

17. A method of treating hair comprising:
applying to hair the composition of claim 1; and
performing a first rinse with water.

18. The method according to claim 17, further comprising:
applying a conditioner composition; and
performing a second rinse with water.

* * * * *